United States Patent [19]

Ingalz

[11] 4,243,322
[45] Jan. 6, 1981

[54] METHOD AND APPARATUS FOR PHOTOLUMINESCENT DETECTION AND MEASUREMENT

[75] Inventor: Thomas J. Ingalz, San Jose, Calif.

[73] Assignee: International Diagnostic Technology, Santa Clara, Calif.

[21] Appl. No.: 899,545

[22] Filed: Apr. 24, 1978

Related U.S. Application Data

[63] Continuation of Ser. No. 703,578.

[51] Int. Cl.³ ............... G01N 21/01; G01N 21/09
[52] U.S. Cl. ............... 356/244; 250/429; 356/246; 250/461 B;576
[58] Field of Search ............... 356/85, 244, 246; 23/253 R, 259, 292; 250/432 R, 429

[56] References Cited

U.S. PATENT DOCUMENTS

| | | | |
|---|---|---|---|
| 3,359,973 | 12/1967 | Hoffman | 23/253 R |
| 3,937,614 | 2/1976 | Sodickson | 250/461 |
| 4,014,649 | 3/1977 | Kiesow | 23/253 R |
| 4,025,310 | 5/1977 | Bolz et al. | 23/230 B |

FOREIGN PATENT DOCUMENTS 390442  11/1973  U.S.S.R. ............... 250/461 B

*Primary Examiner*—John K. Corbin
*Assistant Examiner*—W. H. Punter
*Attorney, Agent, or Firm*—Limbach, Limbach & Sutton

[57] ABSTRACT

A photoluminescent system to determine the kind and amount of photoluminescent-labelled sample, such as derived from biological fluid, in which the labelled sample is coated onto a surface of an elongate carrier member. Such member is inserted into a quiescent light-tight enclosure at which the exposed side is impinged upon by illumination radiation and the radiation emitted therefrom is collected from the same exposed side.

3 Claims, 6 Drawing Figures

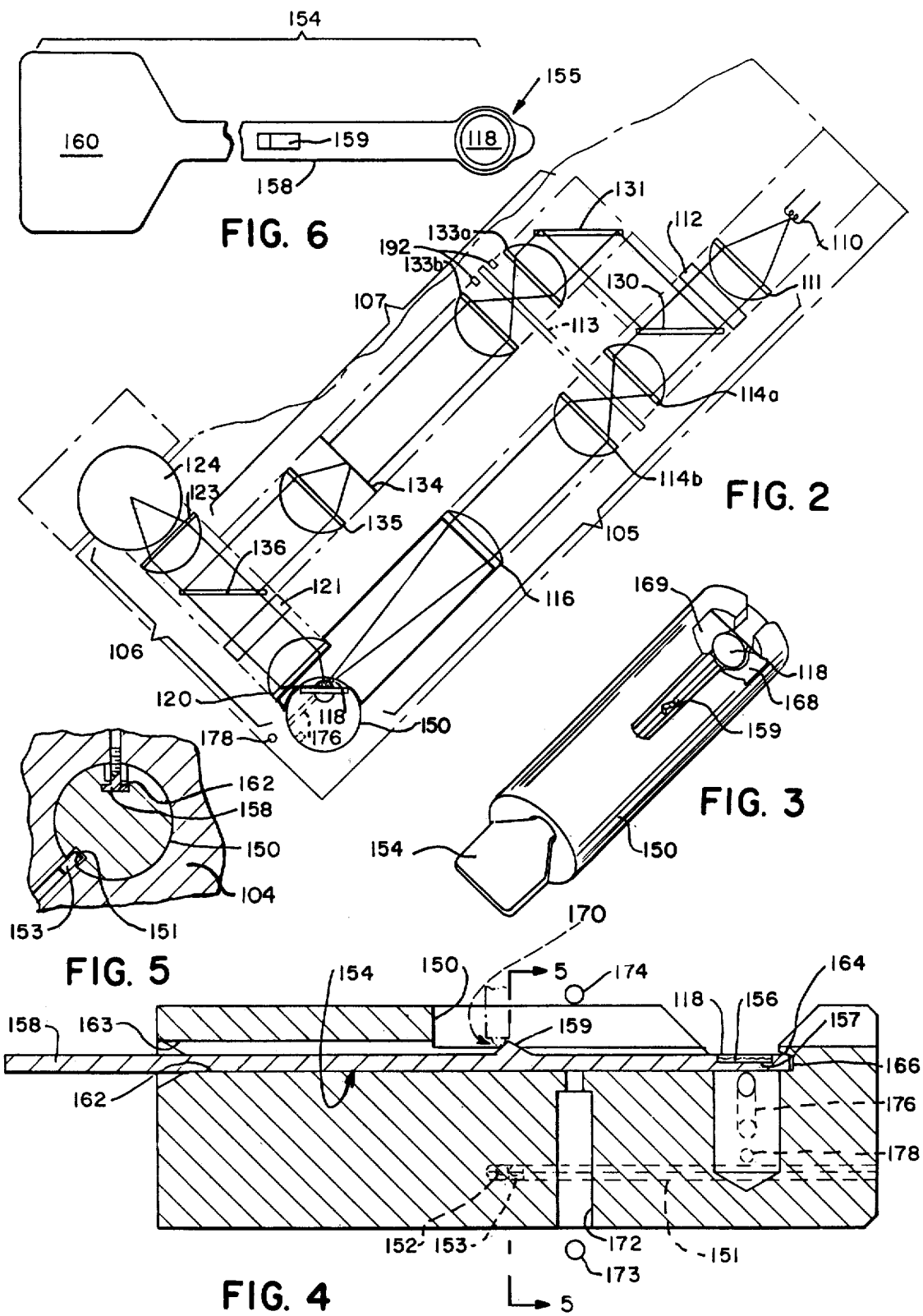

4,243,322

METHOD AND APPARATUS FOR PHOTOLUMINESCENT DETECTION AND MEASUREMENT

CROSS-REFERENCE TO RELATED APPLICATIONS

This is a continuation application of U.S. application Ser. No. 703,578 filed July 8, 1976, which is now abandoned.

Reference is made to a patent application in the name of Richard A. Harte, entitled "Fluorometric System, Method and Test Article", Ser. No. 703,579, filed simultaneously herewith, now U.S. Pat. No. 4,056,724, and Ser. No. 627,941, filed Nov. 3, 1975, now U.S. Pat. No. 3,999,948.

BACKGROUND OF THE INVENTION

This invention relates to a photoluminescent system for the detection of sample substances, as derived from biological fluids or tissue labelled with photoluminescent materials and to fluorometers adapted for accurate measure of such labelled samples on a support surface of a carrier member.

There are many techniques available for the detection of an unknown quantity of a biologically derived sample (e.g., serum or urine). During such techniques, a labelled substance which has reacted with the sample must be separated from the unreacted labelled substances which includes free and non-specifically bound substance. This separation in liquid form is known to be inefficient, unreliable, and tedious. Many solutions have been proposed to solve this problem by the use of diagnostic reagents coated on a solid surface which combine with the labelled substance.

In one technique, reagents are coated upon plastic test tubes by physical adsorption of antibodies specific to the sample substance to be tested. See, e.g., article by Catt et al in the *Journal of Biochemistry*, 1966, Vol. 100, page 31c and in *Science*, Vol. 158, page 1570, 1967. This technique is difficult to control because of the non-uniformity of the plastic surface and imprecision in the coating technique. Furthermore, during washing to remove unreacted labelled substance, a relatively weak physical coating bond holding the antibodies can be disrupted resulting in their loss along with reacted labelled substance. Also, this technique requires a separate procedure for the coating of each test tube. This would be particularly time consuming, especially to insure reproducibility, if covalent attachment were employed to prevent the loss of diagnostic reagent. In addition, such test tube coating does not lend itself to the precise viewing required in a solid front surface fluorometric system. Furthermore, use of a test tube restricts covalent attachment to the material of construction used in making the tube.

Another solid surface approach is set forth in Bratu, Jr., et al U.S. Pat. No. 3,826,619. This system employs a physically adsorbed diagnostic reagent coated on the tip of a holder. This tip is first fitted into a receptacle for the sample and then into a receptacle for the labelled substance. This system is subject to inaccuracies because of losses in rubbing of the unprotected tip against the close fitting receptacle. Also, there is no ability to stir the tip in the receptacle leading to long incubation periods. Additionally, this technique does not lend itself to reproducible mass production as each holder must be individually coated with diagnostic reagent. Furthermore, it is undesirable for precise viewing.

An improved solid surface system is described in Deindoerfer et al patent application, Ser. No. 627,941, filed Nov. 3, 1975. In a preferred embodiment, a disc bearing a fluorescently-labelled diagnostic reagent is carried by an elongate holder and inserted into a viewing housing of a fluorometer for precise positioning of the disc. However, the disc is not essentially isolated from the remainder of the fluorometer or the environment. Therefore, if the fluorescent label on the disc is read while coated with a liquid layer, it is subject to evaporative cooling. As it is known that the intensity of a fluorescent signal is dependent on temperature, such cooling would cause a drift in signal. If the evaporation is sufficient to cause the liquid layer to become discontinuous, this produces an additional source of signal drift based upon a modification of the optical characteristics of the surface. The advantages of reading the surface while wet are set forth in the copending Bolz et al patent application, Ser. No. 690,975, entitled "Method for Reading a Wet Fluorescent Surface", filed May 28, 1976, now U.S. Pat. No. 4,025,310, and are summarized hereinafter.

SUMMARY OF THE INVENTION AND OBJECTS

The apparatus of the present invention analyzes a sample by photoluminescent techniques. The sample is supported as an exposed layer by a surface portion of an elongate carrier member. The carrier member is inserted into a quiescent enclosure substantially isolated from atmospheric conditions and preferably light-tight. The apparatus includes an optical system for delivering excitation radiation to the exposed side of the sample surface and a photoluminescent collector which receives the illumination emitted from the same exposed side. The surface is read while coated with an aqueous film. The quiescent enclosure about the carrier member during reading minimizes evaporation of the aqueous film.

It is an object of the invention to provide an apparatus particularly adapted for precisely positioning the sample containing carrier member for viewing by a fluorometer.

It is another object of the invention to provide an apparatus of the foregoing type in which the sample surface of the carrier member is substantially isolated from ambient atmospheric conditions.

It is another object of the invention to provide an apparatus of the foregoing type which is substantially light-tight with the carrier member in an inserted position.

It is a further object of the invention to provide a method for reading a sample coated onto a carrier member and covered with a continuous aqueous film while enclosed in an apparatus of the foregoing type.

It is another object of the invention to maintain the sample surface in an isotherm condition to minimize drift.

Further objects and features of the invention will be apparent from the following description of the preferred embodiments taken in conjunction with the accompanying drawings.

BRIEF DESCRIPTION OF THE DRAWINGS

FIG. 2 is an optical diagram of the fluorometer of FIG. 1.

FIG. 3 is a prospective view of a test stage assembly including a sample holder constructed in accordance with the present invention and particularly adapted for use in the fluorometer of FIG. 1.

FIG. 4 is a cross-sectional view, in elevation, of the test stage assembly of FIG. 3.

FIG. 5 is a cross-sectional view taken along the line 5—5 of FIG. 4.

FIG. 6 is a top plan view of the sample holder of FIG. 2.

DETAILED DESCRIPTION OF THE PREFERRED EMBODIMENTS

Figure 1:
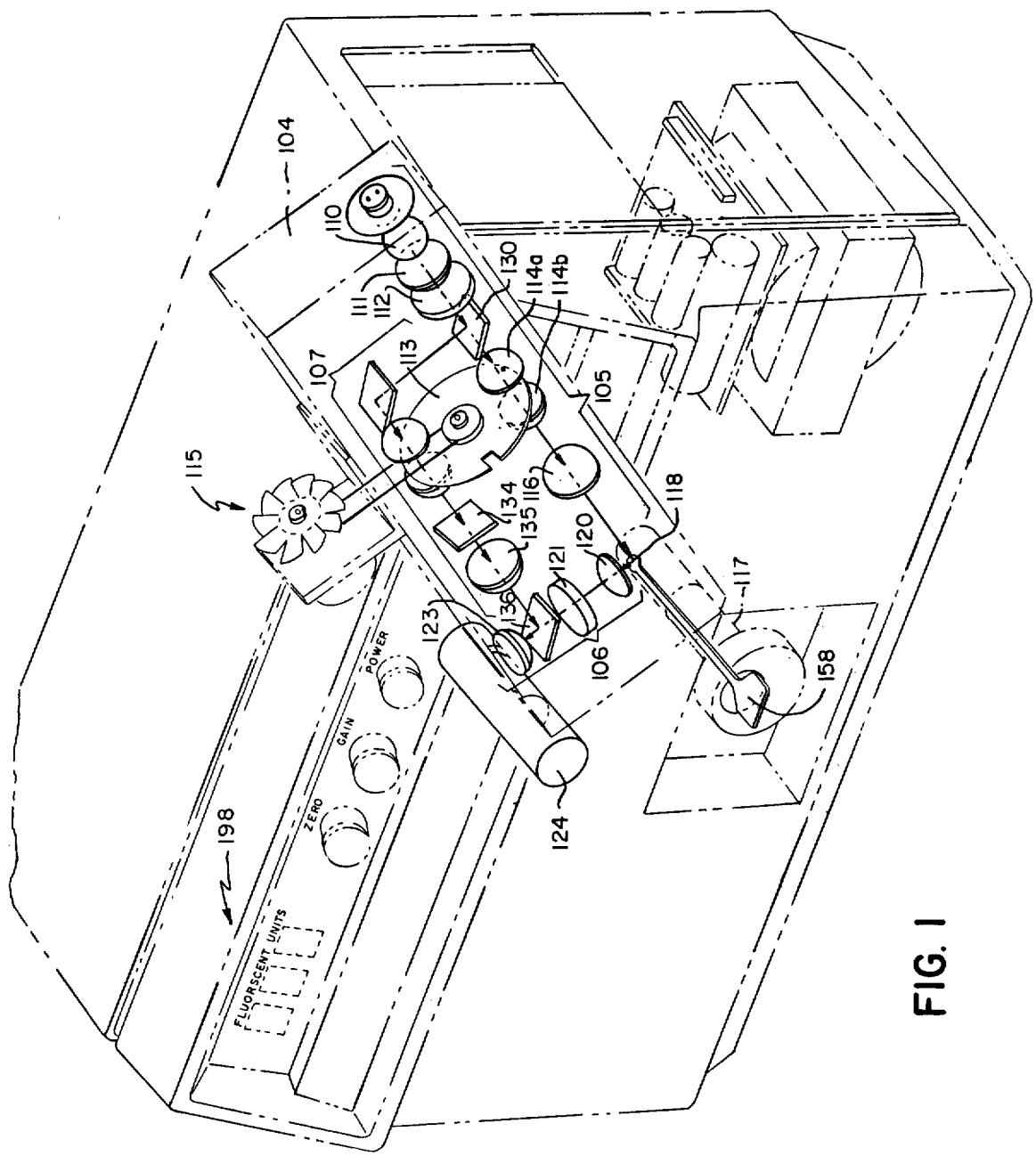
FIG. 1 is a schematic cross-sectional view of a fluorometer constructed in accordance with the present invention shown with external portions in phantom lines.

The present invention relates to a photoluminescence detection system and method to quantitatively detect and measure a photoluminescent sample substance coated as a layer on a surface of a carrier member. The term "photoluminescence" includes within its scope fluorescence and phosphorescence. A fluorometer is employed to measure both types of emissions. As defined herein, the term "photoluminescent labelled sample substance" is one which includes a material derived from either a biological fluid or tissue and which, alone, or in combination with other materials, emits photoluminescence as a result of excitation with a selected wavelength of light in a solid layer form.

Referring to FIG. 1, there is shown such a lens type fluorometer, the overall outward appearance of which is shown in phantom lines. The optical system of the fluorometer is developed within an opaque block 104 of plastic, as for example, Delrin, selected because of its dimensional and thermal stability. Also, Delrin has low thermal conductivity and so provides excellent thermal insulation to the stage surrounding the sample surface to maintain it in an isothermal condition to minimize fluorescent drift due to temperature variation. The block is machined to accept the various components as shown in the drawings. The details of the machining are not believed essential to understanding the invention and, accordingly, they have been omitted for the sake of clarity.

Referring simultaneously to FIGS. 1 and 2, the system generally consists of three major optical systems: an illumination optical system 105 for supplying excitation light to the sample; a collection optical system 106 for receiving fluorescent output from the sample; and a reference level optical system 107 for periodically establishing and checking zero and preset intensity levels.

The illumination optical system 105 consists of lamp 110, condensing lens 111, excitation filter 112, chopper 113, and its lens system 114a and 114b, as driven by an electric synchronous motor 115 and focusing lens 116 for imaging excitation light onto a test stage 150 including sample 118.

The collection optical system 106 consists of a collecting lens 120, emission filter 121, and photodetector lens 123 which images the sample member surface onto a photodetector 124.

The reference level optical system 107 consists of a beam-splitter 130, a turning mirror 131, chopper 113 and associated reference lens systems 133, a diffusing screen 134, a portion of which is developed by lens 135 and re-inserted at beam splitter 136 into the collection optical system 106. Rotation of the chopper 113 causes light to pass alternately through the illumination optical system 105 or through the reference optical system 107. Thus the output at the detector is an alternating signal during one period of which the intensity of the excitation source is measured while the other period measures the fluorescent output.

Many of the optical components shown and described herein could be selected from a wide variety of available more complex designs, but the following have been found to be particularly satisfactory for use in the present invention. All of the lenses are of aspheric type and are standard products of Mells Griot, product 01 LAG 005. These lenses have f/0.75 and are planar on the non-aspheric side. Lens 120 which collects the light from the sample station is the only lens for which a substitution is not readily available in view of the large aperture and solid angle of collection required of that lens.

FIG. 2 contains ray tracing lines thereon which serve to illustrate the functions of the lenses and optical components. Thus, lens 111 collimates the light from the light source and passes it in parallel rays through the first filter at 112 after which the beam-splitter 130 divides off a certain portion of the light to be delivered to the reference optical system 107. The remainder passes to the chopper lens pair 114 in the excitation optical system 105. The first lens of this pair 114a focuses the light down to a small spot so that the cut-off and cut-on times and general level of intensity of light exiting from the chopper is well-defined in value over an appropriate period of time. The second lens 114b of that pair collimates the light for delivery to a focusing lens 116 which brings an image of the filament down into a small focused spot on a central area of the sample carrier 118.

The output from the sample is collected by planospheric lens 120 over a wide solid angle and delivered in parallel rays through the emission filter 121, through a beam insertion device 136, and thence focused by detector lens 123 onto the active element of the photodetector 124.

The portion of the beam which is removed for reference purposes is turned by turning mirror 131 to follow a path parallel to and alongside the excitation path. This light is passed through lens pair 133 which also brings the light source to a focus in the plane of the chopper so as to also provide for rapid turn-on, turn-off, and well-defined value of intensity when the reference beam is on. The reference beam is then passed in parallel rays to a diffusing screen 134 which can consist of a film of polyester, such as that made by DuPont (Type A), having a dull matte finish on the side facing the detection system 106. The matte finish serves as a light scattering function and thus converts the film into a secondary or reference source of high uniformity. A portion of the certain area of the film is taken by lens 135 and the rays made parallel for being passed to insertion mirror (partial) 136 lying in the collection stream path between the emission filter 121 and the photodetector focusing lens 123.

Referring now more particularly to FIGS. 3-5, the test stage 150 is shown in detail. This stage 150 is removable in its entirety to facilitate cleaning. The state 150 is inserted into a cylindrical passageway in block 104 at a lowermost position such that the carrier 118 containing the sample thereon faces upwardly and in a substantially horizontal plane within the assembly as a whole. By making this provision, together with certain structural features of the sample carrier, it is possible to insert and measure a sample having a substantially free liquid containing surface while simultaneously maintaining that surface free of changes during analysis (such as by evaporation). The stage is rotationally oriented for insertion into the optical block 104 by virtue of an elongate axial slot 151 formed along one side of the stage and adapted to accomodate a locating pin 153 mounted in the optical block. A similar locating pin 152 projecting in the elongate slot 151 indicates when the stage has been brought to a fully inserted position within the block.

The sample carrier 118 is mounted on a removable sample carrier member in the form of a spatula 154 (shown inserted in FIGS. 3 and 4 and separately in FIG. 6) consisting of an end portion 155 having a substantially planar surface 156 and an area of slight depression 157 formed at that end of the member on which carrier 118 is disposed to form a support for a film or coating of sample. The spatula 154 further consists of an elongate blade 158 having a registry projection 159 thereon and terminates at its other end in a paddle 160 suitable for being easily gripped by the operator. The spatula is easily removed and inserted into the stage, the latter normally remaining in place within the instrument. Thus, an elongate slot in the form of slot 162 is provided within the stage for receiving the carrier, together with an upwardly extending groove 163 which accomodates projection 159. When fully home, the parts appear as shown in FIG. 4. It will be further noted that the outward extremity of the mounting slot 162 (at 164) is provided with a converging wedge-shaped configuration so that when the spatula is fully seated, the end 166 thereof is urged downwardly against the floor of slot 162 into precisely positioned contact within the stage. With the utilization of plastic parts for many of the components, it is found preferable that these components be restrained laterally and in every other dimension so that any slight warpage of the plastic parts of which the carrier member is made is compensated for, the member being urged into exact position against the bottom of slot 162 within the analysis stage.

Consideration of the optical diagram with respect to the focusing of light onto the stage and to the carrier spatula and the collection of light therefrom as shown in FIG. 2 will explain the purpose for the relieved portions 168, 169 provided by the removed portions of the end of stage 150 and laterally located adjacent the sample 118. Once positioned, member 154 is maintained in position by virtue of urging contact made by a resiliently mounted setting member, spring-loaded ball 170, carried in the body 104 of the optical system and adapted to engage and urge the back inclined surface of projection 159 to urge the carrier member inwardly against slot 162 for precise positioning. In addition, ball 170 falls behind that back surface and assumes a position serving together with the projection itself to block light from passing through the slot 162. Such light is capable, if not blocked, of causing non-dark background readings.

An aperture 172 is provided through the stage and passes light from a small light-emitting diode 173 to a small light detector 174. This aperture is closed by the passing of the member 154 as the same is pushed into the unit and when closed provides a "ready" signal for the associated electronics. An additional aperture 176 extends from the region immediately below the sample carrying end of member 154 and in general alignment with the excitation light beam so that a photodetector 178 positioned immediately behind this second aperture indicates when the sample is actually in position and blocking light from the beam.

The importance of precise repeatable positioning of a fluorescent sample carried as a layer on a support surface of a diagnostic reagent holder is illustrated in Example 2 of co-pending application Ser. No. 627,941, filed Nov. 3, 1975. As illustrated there, even relatively minor differences of separation between the lens system and the surface to be measured cause significant differences in the measurement of the fluorescent signal.

It is a particular feature of the present invention that the test stage 150, even though removable together with its independently removable sample carrier member 154, nevertheless when assembled forms both a light-tight and air-tight enclosure within the optical assembly. The former eliminates background light; the latter retards evaporation from an aqueous film over the free sample surface at 118 during the measurement period. The latter generally quiescent enclosure is defined and formed by the carrier member 154 itself which closes aperture 176, by the stage and its close fitting relationship with the adjacent block, and by lens 116 and 120, both of which are sealed into contact within bores supporting the respective excitation and collection optical systems.

The intensity of a fluorescent signal on a surface is highly sensitive to the surface temperature. Thus, to prevent signal drift, it is important to maintain the sample surface in an isothermal condition during reading. This is accomplished by viewing the surface in a quiescent enclosure essentially isolated from ambient atmospheric conditions both within the apparatus external to the enclosure and also external to the instrument. The apparatus may be maintained within a few degrees of room temperature by a cooling fan in the apparatus external to the enclosure. Since the apparatus is formed of a material of low thermal conductivity, such as Delrin, such a small temperature differential is not transmitted to any significant extent into the quiescent enclosure of the test stage.

There are many advantages in reading a fluorescently labelled sample on a solid support surface carrier 118 of spatula 154 while the carrier is coated with a continuous aqueous layer or film. One is that a steady reading without drift is obtained so long as the surface is read prior to evaporation to discontinuity of the aqueous layer. In addition, the presence of the aqueous layer has been found to enhance the optical properties of the surface for transmitting a maximum signal. Furthermore, the last stage in an analytical fluorometric technique normally comprises washing the sample surface with an aqueous liquid. Thus, reading prior to complete drying of the surface speeds up the overall system. It is important to avoid evaporation of the aqueous layer to discontinuity as it is believed that such discontinuity is the cause of drift of the signal. The above factors are fully set forth in the aforementioned co-pending Bolz et al application Ser. No. 690,975, entitled "Method for Reading a Wet Fluorescent Surface", now U.S. Pat. No. 4,025,310.

A number of techniques are set forth in the last-named patent application for maintaining a continuous aqueous film during reading by a fluorometer, such as by reading in a horizontal position or by the use of a humectant. It has been found that the procedure of inserting the aqueous film containing sample support surface of the carrier member into a quiescent enclosure isolated from ambient atmospheric conditions external to the enclosure produces stable readings for significantly longer periods of time than such other techniques. It is believed that this is due to a marked decrease in evaporation of the aqueous film under such quiescent conditions.

Another advantage of reading the wet support surface of the present invention in a quiescent enclosure essentially isolated from the apparatus and the surrounding environment is to avoid evaporative cooling by convective air currents. As set forth above, the intensity of a fluorescent signal is inversely related to temperature. Thus, such evaporative cooling would create a source of upward drift in fluorescent signal.

A suitable technique for analyzing a sample label with a photoluminescent substance on carrier 118 is to deposit the labelled substance on the surface and to coat the same with a continuous aqueous film. Then, such surface end of the carrier member 154 is placed into stage 150 which, together with the illumination means and collection means, forms a quiescent enclosure around the sample. Excitation radiation is impinged upon the sample surface and collected at an optical photoluminescence collection end of the fluorometer while the surface is coated with an aqueous film. The surface is free of any liquid volume contained independently of the surface during reading (as in a test tube). It is apparent that the photoluminescence collection end of the fluorometer is spaced apart from the aqueous film.

When inserted, the elongate blade of spatula 154 serves to substantially fill elongate slot 162 due to close clearances. This not only creates the aforementioned quiescent conditions at the sample end of carrier 150 during reading, but also blocks light which would otherwise pass through the channel. Also, projection 159 from blade 158 blocks groove 163.

What is claimed is:

1. An apparatus for analyzing a sample by photoluminescent techniques comprising:
    a sample being supported as an exposed layer by a surface portion of a carrier member;
    test stage means for supporting said carrier member at an analysis location in said apparatus, said test stage means being provided with an elongate slot adapted to removably receive said carrier member, the end of said slot within said test stage having a stop thereat for establishing the fully inserted position of said carrier member, said test stage means further has a means for urging said carrier member toward said stop in the fully inserted position of said carrier member within said test stage;
    illumination means forming a first optical system intersecting said analysis location for delivering excitation radiation to the sample surface thereat;
    photoluminescent collection means forming a second optical system intersecting said analysis location for receiving photoluminescence emitted from the sample surface thereat;
    said illumination means, collection means and test stage means being constructed and arranged whereby the illumination radiation impinges upon said surface to excite the same and said collection means focuses upon said surface to receive radiation emmitted therefrom from the same exposed side; and,
    means for supporting said illumination and collection means and said test stage means to form therewith a quiescent enclosure about the sample layer contained therein whereby said sample surface is substantially isolated from conditions external to said enclosure.

2. Apparatus as in claim 1 in which said carrier member includes an outward projection intermediate its ends inclined toward the sample support surface, and said urging means comprises a resiliently mounted setting member projecting into said slot at a location to contact said inclined projection and urge the carrier member toward said stop with said carrier member in the fully inserted position.

3. Apparatus as in claim 1 in which said stop is provided with a wedge-like configuration and in which said carrier member is generally planar and is provided with a thickness so as to engage said wedge configuration, the latter being arranged to force said carrier member downwardly into firm engagement to be held within said slot whereby said sample is precisely positioned in said stage.

* * * * *